United States Patent [19]

Smirnov et al.

[11] Patent Number: 5,472,852
[45] Date of Patent: Dec. 5, 1995

[54] ASSAY FOR DETECTION OF SELECTIVE PROTEIN C INHIBITION BY PATIENTS

[75] Inventors: Mikhail D. Smirnov; Charles T. Esmon, both of Oklahoma City, Okla.

[73] Assignee: Oklahoma Medical Research Foundation, Oklahoma City, Okla.

[21] Appl. No.: 121,944

[22] Filed: Sep. 15, 1993

[51] Int. Cl.$^6$ .............................. C12Q 1/56; C12Q 1/00
[52] U.S. Cl. .............................. 435/13; 435/4; 435/7.91; 436/63; 436/69; 436/164; 514/2
[58] Field of Search .............................. 435/4, 7.91, 13; 436/63, 69, 164; 514/2

[56] References Cited

U.S. PATENT DOCUMENTS 4,849,403  7/1989  Stocker et al. .............................. 514/2

FOREIGN PATENT DOCUMENTS

| WO91/02812 | 3/1991 | WIPO | C12Q 1/56 |
| WO92/10586 | 6/1992 | WIPO | C12Q 1/56 |
| WO93/07491 | 4/1993 | WIPO | G01N 33/68 |
| WO93/10261 | 5/1993 | WIPO | C12Q 1/56 |

OTHER PUBLICATIONS

Dostal–Johnson, et al. Clinical Immunology and Immunopathology vol. 54 pp. 309–319 (1990).
Nelsestuen, et al. Biochemistry vol. 17: 2134–2138 (1978).
Mann, et al., "Cofactor proteins in the assembly and expression of blood clotting enzyme complexes," *Ann Rev Biochem* 57:915–956 (1988).
Walker, F. J., "Regulation of activated Protein C by Protein S," *J Biol Chem* 256:11128–11131 (1981).
Nelsestuen, et al., "Equilibria involved in prothrombin– and blood–clotting factor X–membrane binding," *Biochemistry* 16:4164–4171 (1977).
Nelsestuen, et al., "Interaction of vitamin K dependent proteins with membranes," *Biochemistry* 17:2134–2138 (1978).
Schwalbe, et al., "Protein structural requirements and properties of membrane binding by γ–carboxyglutamic acid–containing plasma proteins and peptides," *J Biol Chem* 264:20288–20296 (1989).

Pei, et al., "Specific contribution of different phospholipid surfaces to the activation of prothrombin by the fully assembled prothrombinase," *J Biol Chem* 268:3226–3233 (1993).
Fernlund, et al., "Amino acid sequence of the light chain of bovine Protein C," *J Biol Chem* 257:12170–12179 (1982).
Rauch, et al., "Human hybridoma lupus anticoagulants distinguish between lamellar and hexagonal phase lipid systems," *J Biol Chem* 261:9672–9677 (1986).
Triplett, D. A., "Antiphospholipid antibodies and thrombosis," *Arch Path Lab Med* 117:78–88 (1993).
Marciniak, et al., "Impaired catalytic function of activated Protein C: a new in vitro manifestation of lupus anticoagulant," *Blood* 74:2426–2432 (1989).
Amer, et al., "Impairment of the Protein C anticoagulant pathway in a patient with systemic lupus erythematosus, anticardiolipin antibodies, and Thrombosis," *Thrombosis Research* 57:247–258 (1990).
Simioni, et al., "Letter to the editor: spurious Protein C. deficiency due to antiphospholipid antibodies," *Amer J Hematology* 36:299–300 (1991).
Borrell, et al., "Immunoglobulin fractions isolated from patients with antiphospholipid antibodies prevent the inactivation of Factor Va by activated Protein C on human endothelial cells," *Thrombosis and Haemostasis* 68:268–272 (1992).
Freyssinet, et al., "The catalytic role of anionic phospholipids in the activation of protein C by factor Xa and expression of its anticoagulant function in human plasma," *Blood Coagulat and Fibrinolysis* 2:691–698 (1991).
Exner, et al., "Similar mechanism of various lupus anticoagulants," *Thrombosis and Haemostasis* 53:15–18 (1985).

*Primary Examiner*—William H. Beisner
*Assistant Examiner*—Jane Williams
*Attorney, Agent, or Firm*—Richards, Medlock & Andrews

[57] ABSTRACT

An assay useful for detecting the propensity of patients for thrombotic disease, especially patients having the lupus anticoagulant or antiphospholipid antibodies, is described. The assay is conducted on patient and control plasma in the presence and absence of exogenous Protein C with a membrane source comprising phosphatidylethanolamine and phosphatidylserine. Patients at risk exhibit test results indicating activated Protein C function is inhibited.

36 Claims, 7 Drawing Sheets

5,472,852

ASSAY FOR DETECTION OF SELECTIVE PROTEIN C INHIBITION BY PATIENTS

TECHNICAL FIELD

This invention relates to the field of diagnostic testing of persons suspected to be at risk for thrombotic complications.

BACKGROUND OF THE INVENTION

The government may have certain rights in this invention, since it was supported in part by a research grant awarded by the National Institutes of Health.

The blood clotting system is a natural and necessary process which occurs in humans and other vertebrates to seal the circulatory system from blood loss upon injury. The thrombus, or blood clot, forms from a complex cascade of reactions involving a number of plasma glycoproteins. In one of the final steps of clot formation, thrombin is formed by cleavage of prothrombin, which reaction is catalyzed by activated Factor X (Factor $X_a$). Activated Factor V (Factor $V_a$), $Ca^{2+}$ and phospholipid membranes enhance the activity of Factor $X_a$ in activating prothrombin. Thrombin catalyzes formation of fibrin (which polymerizes to form a soft clot) from fibrinogen.

Thrombin catalyzes proteolysis of Protein C which inactivates Factor $V_a$. This feedback mechanism is important because clot formation must be limited in vivo to prevent clots from forming in areas where the body not only does not need them, but where they can possibly cause injuries, such as stroke, heart attack, spontaneous abortions and other thrombotic diseases. These injuries often cause fatalities.

Protein C is a vitamin K-dependent protein plasma zymogen of the anticoagulant serine protease, activated Protein C (also referred to herein as "APC"). Protein C is activated primarily on the surface of endothelium by a complex composed of thrombin and thrombomodulin. Thrombomodulin acts to specifically bind thrombin. Thrombin bound to thrombomodulin thereby obtains a diminished ability to cause clot formation. Thrombin bound to thrombomodulin also obtains increased capacity to activate Protein C. Activated Protein C then functions as an anticoagulant by proteolytically inactivating Factors $V_a$ and $VIII_a$, a process that is enhanced by a vitamin K dependent cofactor, protein S, negatively charged membrane surfaces and $Ca^{2+}$ ions.

One group of patients who are at increased risk for thrombotic diseases are those who have lupus anticoagulants, which are antibodies which bind to anionic phospholipids used in clotting assays based on the PTT (partial thromboplastin time) or APTT (activated partial thromboplastin time) techniques. See The Merck Manual (16th Ed. 1992) at 1225; J. E. Ansell, Handbook of Hemostasis and Thrombosis (Little, Brown & Co., Boston) at 19 (1986). Typical PTT test results for patients having the lupus anticoagulant are a prolonged clotting time that fails to correct with a 1:1 mixture of the patient's and normal plasma, a normal or minimally prolonged PT (prothrombin time), and a nonspecific depression of those clotting factors measured by a PTT technique (Factors XII, XI, IX and VIII). The lupus anticoagulant antibodies may also react with cardiolipin which can interfere with assays utilizing cardiolipin as a reagent. See The Merck Manual, supra. Anti-cardiolipin or anti-phosphatidylethanolamine antibodies can cross react with each other, but not interact with sufficient affinity to procoagulant phospholipids to be anticoagulants. Because of the specificity of phospholipids for activated Protein C, such antibodies would selectively inhibit activated Protein C anticoagulant activity without influencing the coagulation tests performed in the absence of activated Protein C which are used to diagnose the presence of a "lupus anticoagulant."

Despite interference of the lupus anticoagulant antibodies with procoagulant phospholipid in clotting tests in vitro, persons with the antibodies have been reported to have an increased risk for thrombosis, either venous or arterial. Further, repeated spontaneous abortions in the first trimester of pregnancy have also been reported. Id. Patients have been treated with long term anticoagulant therapy to reduce the possibility of thrombosis, but no adequate technique has been developed for monitoring the effectiveness of such therapy. It should also be noted that other patients, who do not necessarily test positively for the lupus anticoagulant, may also be at risk for thrombotic disease. Further, not all persons who have the lupus anticoagulant or other risk factors may have the identical propensity for thrombosis.

In order to attempt to identify patients at risk for thrombosis, standard clotting tests have been performed on patient plasma. Additional testing has been suggested as described above where PTT and/or PT test results do not appear to be normal, such as repeating the test with added normal plasma. However, no technique has been developed to differentiate among lupus patients and among others which patients have the highest propensity to have a thrombotic incident.

In several clotting assays, it has been found beneficial to employ a membrane source to facilitate the reaction. It has been reported that the activity of Factor $X_a$ in activating prothrombin is enhanced many fold in the presence of Factor $V_a$, $Ca^{2+}$ and phospholipid membranes containing phosphatidylserine.

Analysis of the prothrombin activation complex, referred to as prothrombinase, has led to a model in which membrane acceleration of coagulation reactions is considered to be mediated by binding the enzyme, cofactor and substrate to the membrane surface, thereby increasing the local concentration of reactants and enhancing key protein-protein interactions-necessary for optimal catalysis. K. G. Mann et al., Ann Rev. Biochem. 57:915–56 (1988). This model is consistent with that proposed for the Factor $V_a$ inactivation complex. F. J. Walker, J. Biol. Chem. 256:11128–31 (1981). All studies have demonstrated that high affinity binding of these proteins involves negatively charged phospholipid surfaces. G. L. Nelsestuen et al., Biochemistry 16:4164–77 (1977); G. L. Nelsestuen et al., Biochemistry 17:2134–38 (1978); and R. A. Schwalbe et al., J. Biol. Chem. 264:20288–96 (1989). Of the naturally occurring negatively charged phospholipids, phosphatidylserine (also referred to herein as "PS") is the most effective functionally in the prothrombinase complex and in terms of binding interactions with Factors $V_a$ and $X_a$. G. Pei et al., J. Biol. Chem. 268:3226–33 (1993). Taken together, these observations have led most investigators to assume that all of the complexes would share similar phospholipid requirements for optimal function. This assumption gained further support from the fact that $\gamma$-carboxyglutamate (Gla) containing regions of the vitamin K dependent proteins share considerable sequence identity (P. Fernlund et al., J. Biol. Chem. 257:12170–79 (1982)), and it is this domain that is primarily responsible for membrane interaction. Schwalbe et al., supra. Previous investigators have thus assumed that the membrane requirements for inactivation of Factor $V_a$ with activated Protein C would be similar to those required for prothrombinase activity for activation of thrombin.

Surprisingly, it has now been found that phosphatidylethanolamine (also referred to herein as "PE") incorporation into membrane vesicles dramatically enhances APC inactivation of Factor $V_a$ without influencing prothrombinase activity. It has also now been found that patient plasma may be screened by assaying it in a one stage assay in the presence and absence of activated Protein C with a membrane source comprising an effective amount of PE. In employing PE in such assays, patient plasma containing lupus anticoagulants has been found to exhibit prolonged clotting times relative to normal pooled plasma control in the absence of activated Protein C, but to exhibit a clotting time less than normal control plasma in the presence of activated Protein C at appropriate phospholipid concentrations. Thus, by altering the composition of the membrane used in assays, recognition of patients most at risk for thrombosis can be determined and the effectiveness of antiinflammatory drugs used to reduce antibody titers, such as for example Prednisone (17, 21-Dihydroxypregna-1,4-diene-3,11,20-trione), or anticoagulation therapies can be monitored.

SUMMARY OF THE INVENTION

An assay for determining the propensity of a patient for thrombotic disease is described which employs an effective amount of a phospholipid membrane source to bind to the reactants, which phospholipid membrane source has a phospholipid component comprising an effective amount of phosphatidylethanolamine (PE) to provide a differential, detectable effect between normal (control) plasma and plasma from patients having a propensity for thrombotic episodes, and an effective amount of phosphatidylserine (PS) to complement said PE in a clotting assay. Preferably, at least about 10% to about 50% PE and at least about 5% to about 50% PS is employed. More preferably, the PS component is limited to a maximum of 25% by weight of said phospholipid component of said membrane source. In a preferred embodiment, the membrane source comprises a phospholipid component comprising about 40% PE, about 20% PS and about 40% by weight phosphatidylcholine (PC). The phospholipid membrane source is preferably employed in a clotting assay which utilizes a Factor X-activating enzyme from Russell's viper venom wherein clotting is initiated by addition of $Ca^{2+}$. A patient's citrated plasma sample is assayed in the presence and absence of exogenous activated Protein C (APC) and the results compared to those obtained for normal control plasma. Patient plasma which selectively inhibits APC is detected by a prolonged clotting time in the absence of exogenous APC relative to normal controls, which also exhibits a clotting time less than normal control plasma in the presence of exogenous APC at optimal phospholipid concentrations.

DETAILED DESCRIPTION

Figure 1:
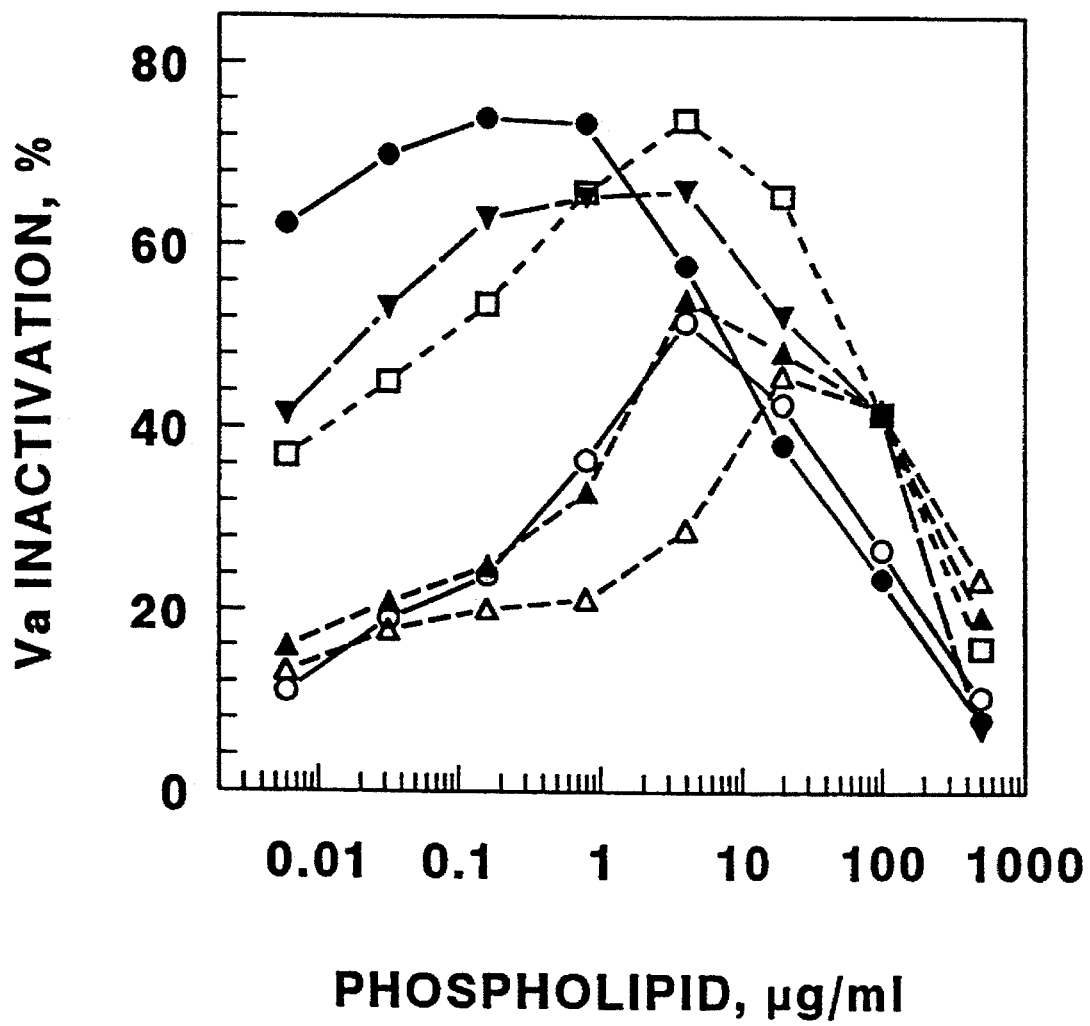
FIG. 1 is a graphical depiction of data concerning the effect of phospholipid composition on inactivation of Factor $V_a$ by APC, where open circles, 20% phosphatidylserine (PS)/80% phosphatidylcholine (PC); closed circles 20% PE/20% PS/60% PC; closed upward pointing triangles, 20% phosphatidylinositol/20% PS/60% PC; open squares, 20% cardiolipin/20% PS/60% PC; open triangles, 20% cholesterol/20% PS/60% PC; and closed downward pointing triangles, 20% phosphatidylglycerol/20% PS/60% PC.

An assay is disclosed which can be used to screen patients for thrombotic propensities.

One component of the assay is a membrane source which is to contain a phospholipid component which comprises an effective amount of phosphatidylethanolamine (PE) to provide a differential, detectable effect between normal (control) plasma and plasma from patients having a propensity for thrombotic episodes and an effective amount of phosphatidylserine (PS) to complement said PE in a clotting assay. Preferably, said phospholipid component comprises from about 10% to about 50% phosphatidylethanolamine (PE), and from about 5% to about 50% phosphatidylserine (PS). The remainder is preferably phosphatidylcholine (PC), but can be selected from any phospholipid which has a head group which is zwitterionic and has no net charge at neutral pH. Preferably, the PS component is from about 5% to about 25% of the phospholipid component. In a most preferred embodiment, the phospholipid component of the membrane source comprises about 40% PE, about 20% PS and about 40% PC by weight of the phospholipid component.

The membrane source is preferably employed in the form of phospholipid vesicles. Such vesicles can be made by any methodology and can be of any size and form. One form of suitable vesicles are sonicated vesicles (SV). These can be, for example, prepared by a modification of published methods. See, e.g., Y. Barenholz, Biochemistry 16:2806–10 (1977). In a preferred method, lipids (1 mg/ml) were suspended by vortexing in 20 mM Tris-HCl, 150 mM NaCl, 0.02% sodium azide, pH 7.4 (TBS) before they were sonicated (Bronson Sonic Power Co, model 350) for 20 min in an ice bath under argon flow at 20% power setting. After sonication, suspensions were centrifuged at 8000× g for 15 min and passed through a 0.22 μm Millipore filter. About 95–99% of initial phospholipid was recovered. When the vesicles were stored, they were kept at 4° C. under argon and resonicated for 5 min immediately before use. Storage did not alter vesicle activity.

In another preferred method, large phospholipid vesicles (LV) were prepared by dialysis from octyl glucoside. L. T. Mimms et al, Biochemistry 20:833–40 (1981). Phospholipids, dried under argon and lyophilized overnight, were suspended in 0.16M octyl-glucoside in TBS at 5 mg/ml to give a detergent to phospholipid molar ratio of 25:1. Suspensions were vortexed 1 min, sonicated in a Branson Ultrasonic labware cleaner (model B3) for 10 min and dialyzed against 4×2 liters of TBS at 4° C. for 2 days. Dialyzed suspensions were centrifuged at 8000× g for 15 min and passed through a 0.22 μm filter. LV phospholipid recovery was 95–98%. LV were either used immediately or stored up to 5 days at +4° C. under argon. Stored LV were vortexed 1 min before use.

Extruded large phospholipid vesicles were prepared by published methods. R. W. Jackman, et al., Proc. Natl. Acad. Sci. (USA) 83:8834–38 (1986). Briefly, dried phospholipid mixtures were suspended at 1 mg/ml in TBS, vortexed 10 min and passed three times through 0.22 μm Nucleopore polycarbonate filter. About 95% of initial phospholipid was recovered in the final vesicle suspension. These vesicles were used immediately.

Recovery in all cases was monitored by employing tracer levels of $^{14}$C-PC in the preparations, such as 1-palmityl-2-[1-$^{14}$C-oleyl] PC (New England Nuclear Products). Phospholipid content can be measured by other methods, such as described by G. R. Bartlett et al., J. Biol. Chem. 234:466–68 (1959). However, it is not necessary to follow yields routinely, given the high recoveries observed.

Electronic microscopy was performed as previously described in L. T. Mimms, supra with minor modifications. Suspensions of phospholipid vesicles were diluted with TBS to 0.1 mg/ml and mixed with an equal volume of 2% of osmium tetroxide in water for fixation. After 20 min, 3 μl of fixed samples were applied to carbon coated grids, incubated 20 min, washed with water, washed 1 min with 2% uranyl acetate in water for negative staining, washed with water and dried on air. A JEOL-JEM-1200 EX electron microscope was used. A standard grid was applied each day to control for microscope magnification. Vesicle size was determined from the photo-micrographs.

The assay for selectively detecting activated Protein C inhibition by a patient sample plasma is conducted utilizing the membrane source described above. A blood sample is collected from the patient into citrate anticoagulant and the citrated plasma is prepared therefrom, according to standard techniques. In a preferred embodiment, clotting times are determined in a one-stage clotting assay performed in the presence and absence of human activated Protein C, which is prepared according to F. B. Taylor, Jr. et al., J. Clin. Invest. 79:918–25 (1987) the disclosure of which is hereby incorporated by reference. The assay is conveniently performed at 25° C. in wells of a 96-well PVC plate (Costar) coated with a mixture of ovalbumin and gelatin to minimize adsorption on the walls, however any appropriate reaction chamber may be utilized which will allow thorough mixing of the components and which is inert to the reactants. About 10 μl of patient citrated plasma and about 10 μl normal control plasma per each 70 μl final reaction mixture is added to the test wells and about 20 μl normal control plasma is added to control wells per each 70 μl final reaction mixture.

Alternatively, the assay may be run without addition of normal plasma to the test sample, however under some conditions the normal plasma addition would be desirable to facilitate clotting.

From about 0.1 to about 3.0 micrograms per ml of activated Protein C (APC) is added to the wells containing a sample of patient plasma and to the other wells containing normal control plasma being run in parallel with the patient plasma. Most preferably, a concentration of 1.0 micrograms per ml APC is utilized. No APC is added to an approximately equal number of wells containing patient plasma or control plasma.

To each well, a membrane source described above comprising about 0.2 micrograms/ml to about 1 milligram/ml total phospholipid is added. Optimal phospholipid may be determined by a dose-response assay. The optimal phospholipid (PL) concentration is that concentration which permits patient plasmas known to inhibit APC function to exhibit a shorter clotting time than normal plasma in the presence of said PL and APC. About 1 nanogram per ml Factor X-activating enzyme from Russell's viper venom (C. T. Esmon, Dissertation, Washington University, St. Louis (1973)) is also added to form the reaction mixture. Factor X-activating enzyme is also available commercially. (American Diagnostic) Clotting is initiated by addition of 25 microliters of 20 mM $CaCl_2$ per each 70 microliter reaction mixture described above. Any $Ca^{2+}$ source equivalent to $CaCl_2$ may be used. Clotting times are determined in a V-max Kinetic Microplate Reader, (Molecular Devices, Menlo Park, Calif.) which measures the rapid increase in turbidity as an increase in OD at 405 nm and time until the rate of change is maximal (time to Vmax). This is recorded as a measurement of time to clot.

The precise amounts of the reagents described can be varied given this disclosure for different desired sample volumes. In place of Factor X-activating enzyme from Russell's viper venom, any activator of Factor X (or Factor $X_a$ itself) may be utilized. Contact activation of coagulation, Tissue Factor, Factor $IX_a$ or $XI_a$ may be used.

Clotting time may be measured by manual assays, in which clotting is observed without the aid of instrumentation, or by instrumentation, which may be automated, which is capable of detecting formation of clots. Suitable instrumentation for example would detect clotting by changes in turbidity at an appropriate wavelength, changes in color in a chromogenic assay for thrombin generation, or any other suitable parameter.

The clotting times of the patient samples are compared to those of the normal controls. In the presence of a membrane source containing PE, those patient samples which exhibit normal or prolonged clotting times in the absence of activated Protein C, but which exhibit shorter clotting times in the presence of activated Protein C are considered to represent a high risk of selective inhibition of the Protein C pathway and consequent risk for thrombotic disease.

Example 1: One Stage Clotting Assay to Screen
Patient Plasma Samples for Risk of Thrombotic
Disease (Variable Phospholipid Concentration)

Phospholipid vesicles containing 40% PE/20% PS/40% PC were prepared according to a standard technique.

A 70 microliter reaction mixture was formed in each of a series of wells of a PVC plate. The reaction mixture contained 30 μl phospholipid vesicles to provide a concentration of total phospholipid of from 0.1 to 300 μg/ml, 10μl of 15 nanograms/ml Factor X-activating enzyme from Russell's viper venom, 10 μl citrated plasma under investigation, and 10μl standard human plasma pool control. Ten μl of 16 nM activated human Protein C was added to one-half of the test wells. In parallel, 70 microliter reaction mixtures were prepared with 20 μl normal pooled control plasma.

Figure 5:
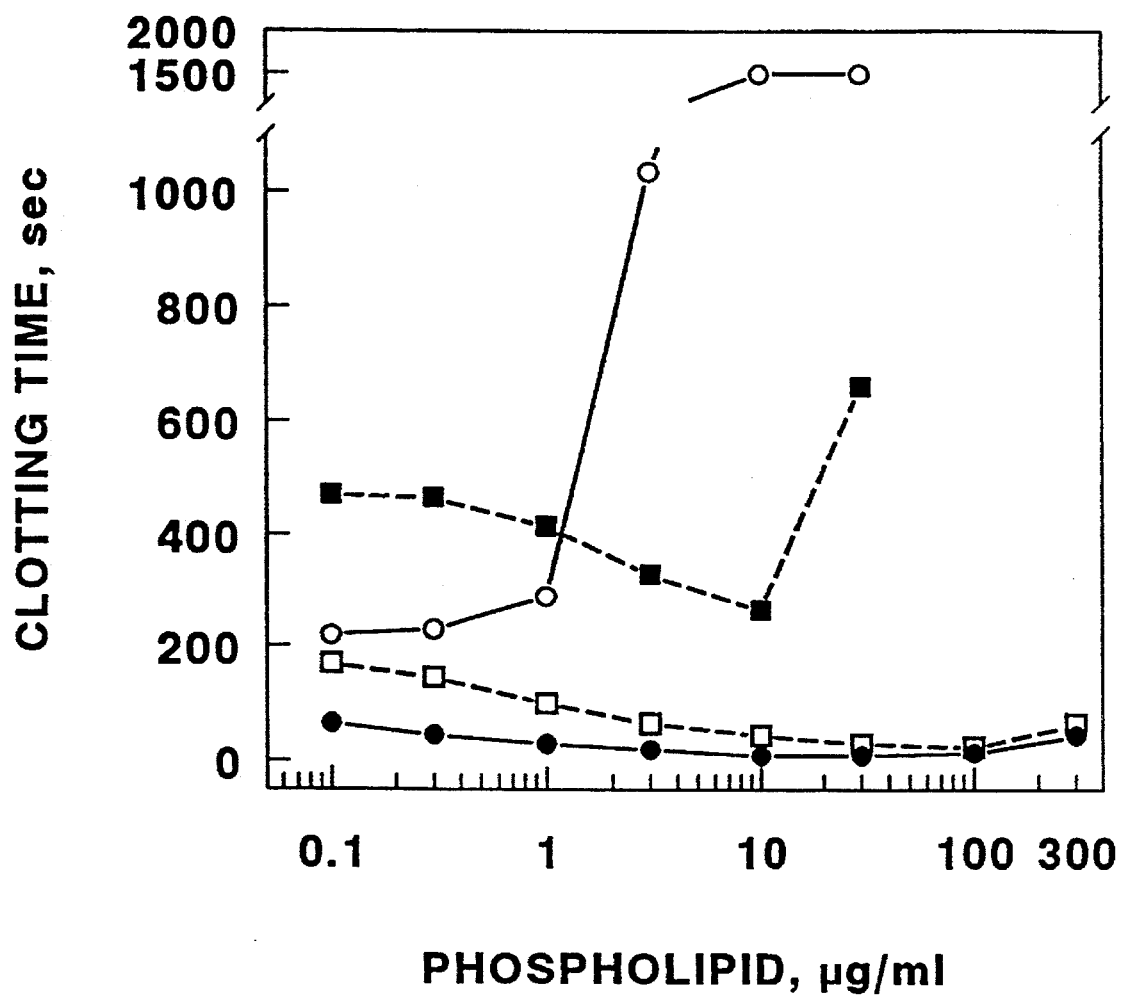
FIG. 5 is a graphical depiction of data concerning the effect of human APC on clotting of normal plasma and plasma from a patient with thrombosis and a lupus anticoagulant as a function of phospholipid concentration where closed circles, normal human pooled plasma without APC; open squares, plasma from a patient with thrombosis and a lupus anticoagulant without APC; open circles, normal human pooled plasma with APC; closed squares, plasma from a patient with thrombosis and a lupus anticoagulant with APC.

Clotting was initiated with 25μl of 20mM $CaCl_2$ and monitored on a V-max Kinetic Microplate Reader at room temperature. The results, shown in Table 1, can graphically be seen in FIG. 5. The data showed that lupus anticoagulants can enhance coagulation on PE liposomes in the presence of APC. For example, at 3 μg/ml phospholipids, the clotting time for "Lupus+APC" is dramatically lower than that of normal control patients.

Figure 6:
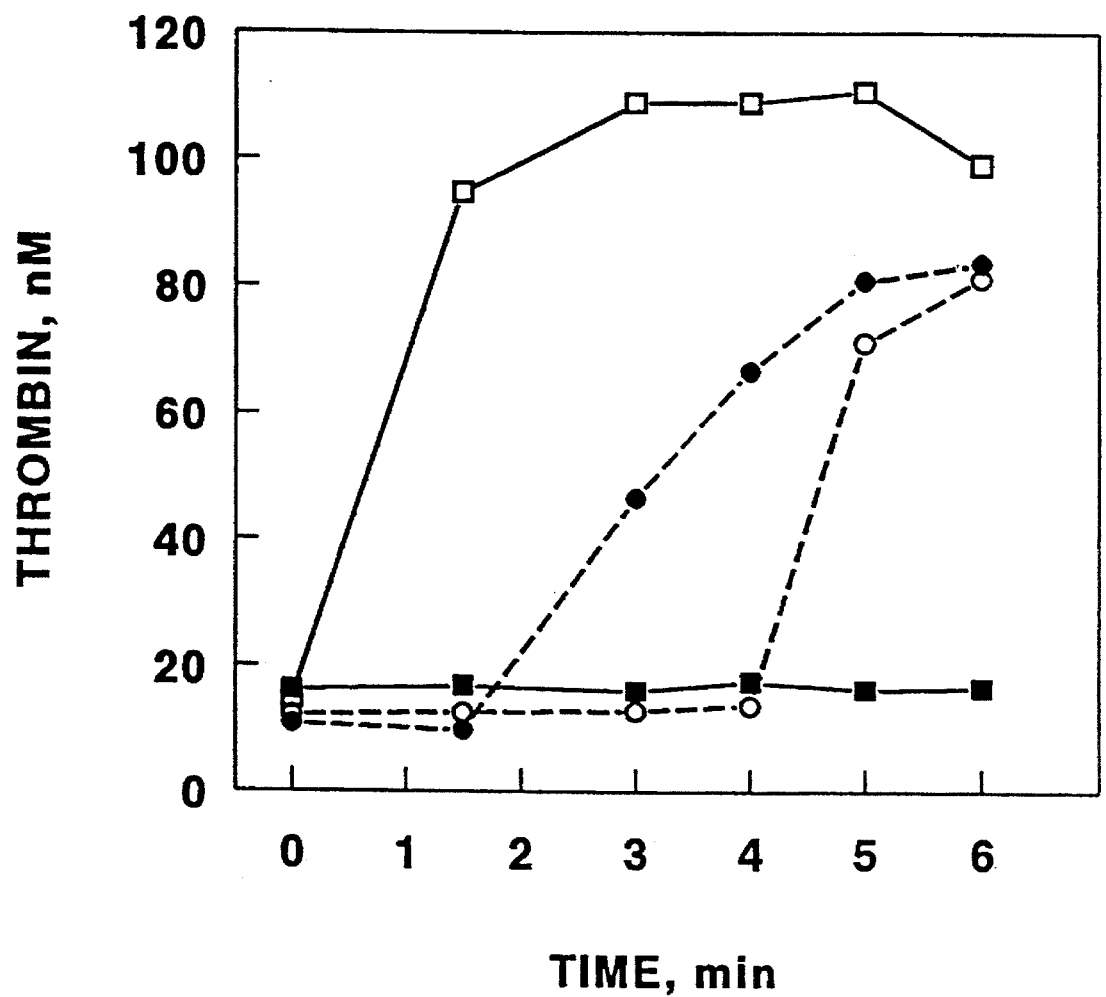
FIG. 6 is a graphical depiction of data concerning thrombin formation differences between normal plasma and plasma containing lupus anticoagulants, in the presence and absence of APC where open squares, normal human pooled plasma without APC; closed circles, plasma from a patient with thrombosis and a lupus anticoagulant without APC; closed squares, normal human pooled plasma with APC; open circles, plasma from a patient with thrombosis and a lupus anticoagulant with APC.

Example 2: Thrombin Formation Differences Between Normal Plasma and Lupus Anticoagulant Plasma in the Presence and Absence of Activated Protein C Kinetics of prothrombin activation with and without 8 nM APC in normal plasma and plasma from a patient with thrombosis and a lupus anticoagulant was tested. The mixture containing 10 μl human plasma under investigation, 10 μl TBS-Gelatin (0.1%) and 10 μl of APTT reagent (Sigma) were incubated for 5 min at 25° C. Then 10 μl of bovine APC (5 μg/ml), 10 μl bovine PS (70 μg/ml) and 10 μl of normal pooled human citrated plasma were added. After a 3 min incubation, prothrombin activation was initiated by addition of 20 μl of 25 mM $CaCl_2$. At the times indicated on the abscissa of FIG. 6, 20 μl of 50 mM EDTA, 200 mM MOPS, pH 7.4 was added to stop the reaction. The zero time point was determined by the addition of EDTA before the $CaCl_2$. Thrombin concentration was determined by the addition of 50 μl of 0.5 mM Spectrozyme -PCa as a substrate for thrombin and the rates of hydrolysis were analyzed on a V-max Kinetic Microplate Reader at room temperature. The results of this example can be seen in Table 2 and in FIG. 6.

Thrombin was found to be generated earlier and to a greater level in lupus patient plasma than in control plasma in the presence of APC.

TABLE 1

COAGULATION ON PHOSPHATIDYL ETHANOLANINE LIPOSOMES IN THE PRESENCE AND ABSENCE OF ACTIVATED PROTEIN C (APC): LUPUS PATIENT VS. CONTROL

| | Clotting Times (seconds) | | | |
|---|---|---|---|---|
| $PL^a$ (μg/ml) | $Control^b$ (−APC) | Lupus (+APC) | Control (+APC) | Lupus (+APC) |
| 0.1 | 65 | 170 | 220 | 470 |
| 0.3 | 45 | 145 | 230 | 465 |
| 1 | 30 | 100 | 290 | 415 |
| 3 | 20 | 65 | 1035 | 330 |
| 10 | 10 | 45 | ≧1200 | 265 |
| 30 | 10 | 30 | ≧1200 | 660 |
| 100 | 15 | 25 | ≧1200 | ≧1200 |
| 300 | 45 | 65 | ≧1200 | ≧1200 |

[a]PL = total phospholipid concentration; phospholipid vesicles containing 40% phosphatidyl ethanolamine, 20% phosphatidyl serene, and 40% phosphatidyl choline.
[b]Control - standard human plasma pool.

TABLE 2

THROMBIN FORMATION IN THE PRESENCE AND ABSENCE OF ACTIVATED PROTEIN C (APC): LUPUS PATIENT VS. CONTROL
[Thrombin] (nanomolar)

| Time (minutes) | $Control^a$ (+APC) | Lupus (+APC) | Control (−APC) | Lupus (−APC) |
|---|---|---|---|---|
| 0 | 16.3 | 12.2 | 14.7 | 10.8 |
| 1.5 | 16.9 | 12.6 | 94.7 | 9.8 |
| 3 | 16.1 | 12.8 | 108.9 | 46.6 |
| 4 | 17.6 | 13.7 | 108.9 | 66.7 |
| 5 | 16.3 | 71.1 | 110.7 | 80.8 |
| 6 | 16.7 | 81.3 | 99.1 | 83.6 |

[a]Control standard human plasma pool.

Figure 4:
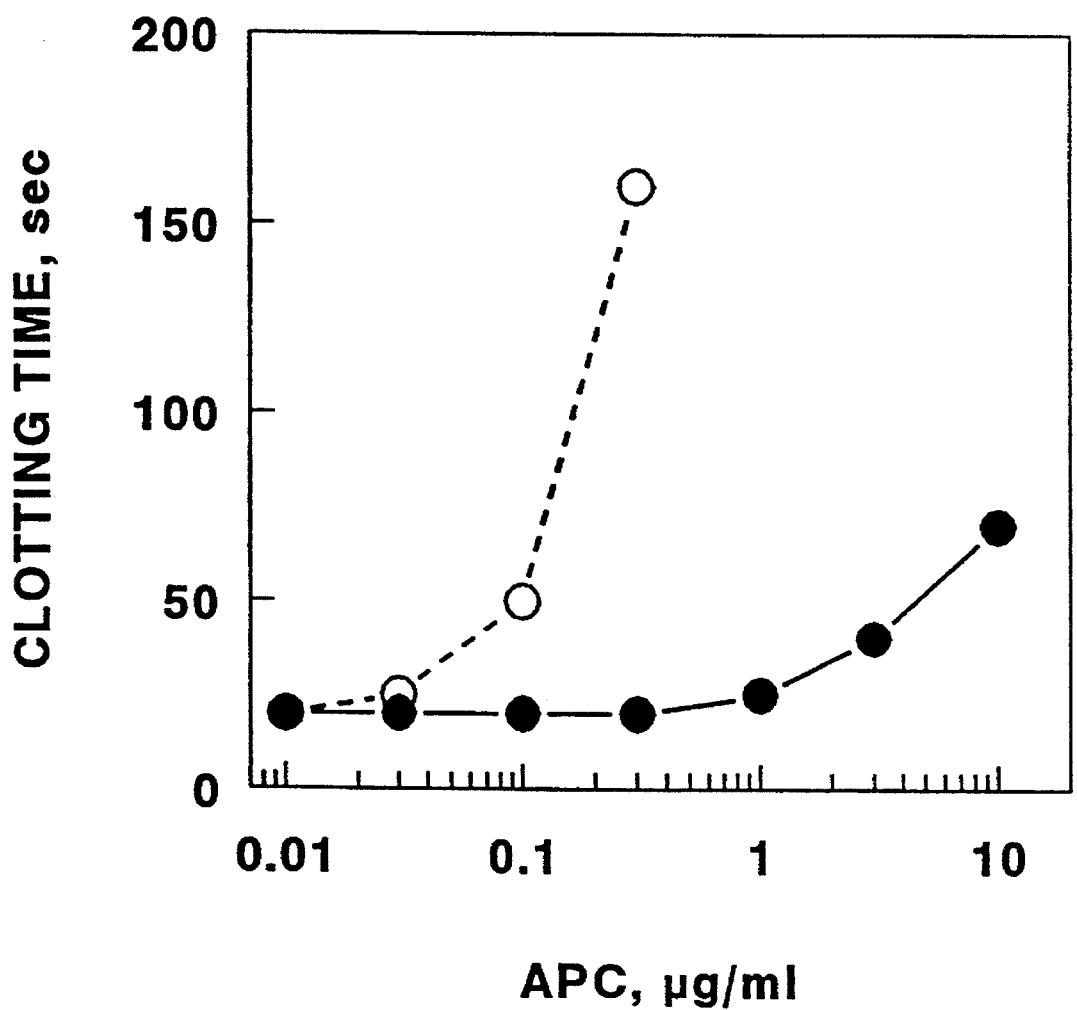
FIG. 4 is a graphical depiction of data concerning the effect of PE incorporation into PS/PC vesicles on APC anticoagulant activity in plasma where sonicated vesicles; closed circles, 20% PS/80% PC; open circles, 40% PE/20% PS/40% PC.

Example 3: The Effect Of PE Incorporation Into PS/PC Vesicles on APC Anticoagulant Activity In Plasma Sonicated vesicles (SV) containing 20% PS/80% PC (10 μg/ml) or SV containing 40% PE/20% PS/40% PC (10 μg/ml) were employed to support the one stage clotting assay in the presence or absence of varying concentrations of human APC. Experimental mixtures (70 μl total before addition of $CaCl_2$) contained variable concentrations of human APC, 10 μg/ml total phospholipid, factor X-activating enzyme from Russell's viper venom (1 nanogram/ml for PE/PS/PC and 10 nanogram/ml for PS/PC) and standard human plasma pool (20 μl). The amount of Russell's viper venom added to each test sample was adjusted to produce the same clotting time for the test sample without APC. Clotting was initiated by addition of 25 μl of 20 mM $CaCl_2$. Clotting times were determined in a V-max Kinetic Microplate Reader. Table 3 shows the data from this experiment and FIG. 4 depicts the data obtained graphically. The experiment indicated that incorporation of PE into vesicles had an effect on APC activity as clotting times increased relative to assays using PS/PC vesicles.

TABLE 3

ANTICOAGULATION ACTIVITY OF ACTIVATED PROTEIN C (APC) IN PLASMA: PE INCORPORATION INTO PS/PC $VESICLES^a$

| | Clotting Time (seconds) | |
|---|---|---|
| APC (μg/ml) | PS/PC (10 μg/ml) | PE/PS/PC (10 μg/ml) |
| 0 | 20 | 20 |
| 0.01 | 20 | 20 |
| 0.032 | 20 | 25 |
| 0.1 | 20 | 50 |
| 0.32 | 20 | 160 |
| 1 | 25 | ≧1200 |
| 3.2 | 40 | ≧1200 |
| 10 | 70 | ≧1200 |

[a]PS/PC = 20% phosphatidyl serine and 80% phosphatidyl choline; PE/PS/PC = 40% phosphatidyl ethanolamine, 20% phosphatidyl serine, and 40% phosphatidyl choline.

Example 4: Coagulation on PE Liposomes in the Presence or Absence of APC At Various Concentrations An assay essentially as described in Example 1 was conducted. The parameters tested on control plasma or plasma from a person with lupus anticoagulant antibodies were various phospholipid (PL) concentrations, and the presence or absence of various APC concentrations. Table 4 provides the data which shows prolonged clotting time of Lupus plasma in the absence of APC, but a decrease in clotting time at 3 µg/ml PL for Lupus plasma plus APC. At 10 µg/ml PL for Control plus APC, the clotting time was so great as to be considered that it would not clot. Optimal [PL] and [APC] can also be determined through such a dose response assay.

and subtracting this value from 1. Thrombin formation was directly proportional to Factor $V_a$ concentration under these conditions.

In the experiments involving inactivation of higher Factor $V_a$ concentration (1 nM, 170 ng/ml) at 4 µg/ml phospholipid, in the second stage the Factor $X_a$ concentration was increased 20 fold (24 ng/ml). In the third stage, after addition of EDTA, the samples were diluted 20 fold before measurement of thrombin activity. At higher Factor $V_a$ concentra-

TABLE 4

CHANGES IN ACTIVATED PROTEIN C (APC) AND PE/PS/PC CONCENTRATIONS: LUPUS PATIENT VS. CONTROL

| PL[a] (µg/ml) | Control[b] (−APC) | Lupus (−APC) | Control (+APC) 0.1 µg/ml | Lupus (+APC) 0.1 µg/ml | Control (+APC) 0.32 µg/ml | Lupus (+APC) 0.32 µg/ml | Control (+APC) 1.0 µg/ml | Lupus (+APC) 1.0 µg/ml |
|---|---|---|---|---|---|---|---|---|
| 0.1 | 65 | 170 | 100 | 235 | 145 | 315 | 220 | 470 |
| 0.3 | 45 | 145 | 80 | 205 | 120 | 280 | 230 | 465 |
| 1 | 30 | 100 | 60 | 160 | 105 | 230 | 290 | 415 |
| 3 | 20 | 65 | 40 | 110 | 100 | 165 | 1035 | 330 |
| 10 | 10 | 45 | 30 | 75 | 120 | 115 | ≧1200 | 265 |
| 30 | 10 | 30 | 30 | 50 | 150 | 100 | ≧1200 | 660 |
| 100 | 15 | 25 | 45 | 85 | 220 | 515 | ≧1200 | ≧1200 |
| 300 | 45 | 65 | 135 | 305 | 500 | ≧1200 | ≧1200 | ≧1200 |

[a]PL = total phospholipid concentration; phospholipid vesicles containing 40% phosphatidylethanolamine, 20% phosphatidylserine, and 40% phosphatidylcholine.
[b]Control standard human plasma pool.

Example 5: Demonstration of Acceleration of Factor $V_a$ Inactivation By Membrane Surfaces Factor $V_a$ inactivation was analyzed with a three stage assay. In the first stage, Factor $V_a$ was inactivated by APC on various membrane surfaces. In the second stage, after inactivation of the APC, residual Factor $V_a$ activity was monitored by adding optimal phospholipid, excess Factor $X_a$ and prothrombin. The resultant thrombin was measured in the third stage using a chromogenic assay. All reagents were diluted in TBS, containing 1 mg/ml gelatin, 1 mg/ml ovalbumin and 10 mg/ml BSA. All stages were performed at 25° C. in the same wells of 96-well PVC plates (Costar), coated with a mixture of ovalbumin and gelatin to minimize adsorption on the walls. The first stage (70 µl) contained variable phospholipid concentration, 10 µg/ml bovine protein S, 7 ng/ml bovine APC, 3.6 mM $CaCl_2$ and 1 ng/ml bovine Factor $V_a$. After 30 min, 10 µl of 160 µM (p-amidinophenyl)methanesulfonyl fluoride was added to inhibit APC. The inhibitor decays rapidly, and in 20 minutes neither APC nor inhibitor activity was detectable. In the absence of APC, Factor $V_a$ activity was stable for at least 1 hour under these conditions. In the second stage, to evaluate residual Factor $V_a$ activity, 4 µg/ml phospholipid (final concentration) was added to all samples containing suboptimal phospholipid, and then Factor $X_a$ (1.2 ng/ml) and prothrombin (100 µg/ml) were added to give the final concentrations indicated. After a 5 min incubation, prothrombin activation was stopped by addition of 10 µl of 50 mM EDTA, 200 mM MOPS, pH 7.4. Thrombin activity was determined with the chromogenic substrate, Spectrozyme-PCa (50 µl, 0.5 mM) on a V-max Kinetic Microplate Reader. Thrombin concentration was determined by reference to a standard curve prepared with human α-thrombin. Percent Factor $V_a$ inactivation was then calculated by dividing thrombin formation in the presence of APC by thrombin formation in its absence tions (10, 100, and 1000 nM), the reactions were run as above except that 4µg/ml of the phospholipid under investigation was employed in the first stage. After inactivation with APC, the sample was diluted to 1 nM active and inactive Factor $V_a$, and phospholipid was added to 4µg/ml. The remainder of the assay was performed as described above.

Experiments were performed with vesicles containing 20% PS, 60% PC, and 20% of one of the following: phosphatidylglycerol, phosphatidylinositol, PE, cardiolipin, or cholesterol. Of these vesicles, those containing PE had by far the largest increase in activity supporting Factor $V_a$ inactivation by APC (FIG. 1), although phosphatidylglycerol and cardiolipin both showed some increased activity in this assay. The presence of PS, or other negatively charged phospholipids were necessary, i.e., PE in combination with PC would not support Factor $V_a$ inactivation effectively.

Figure 2A:
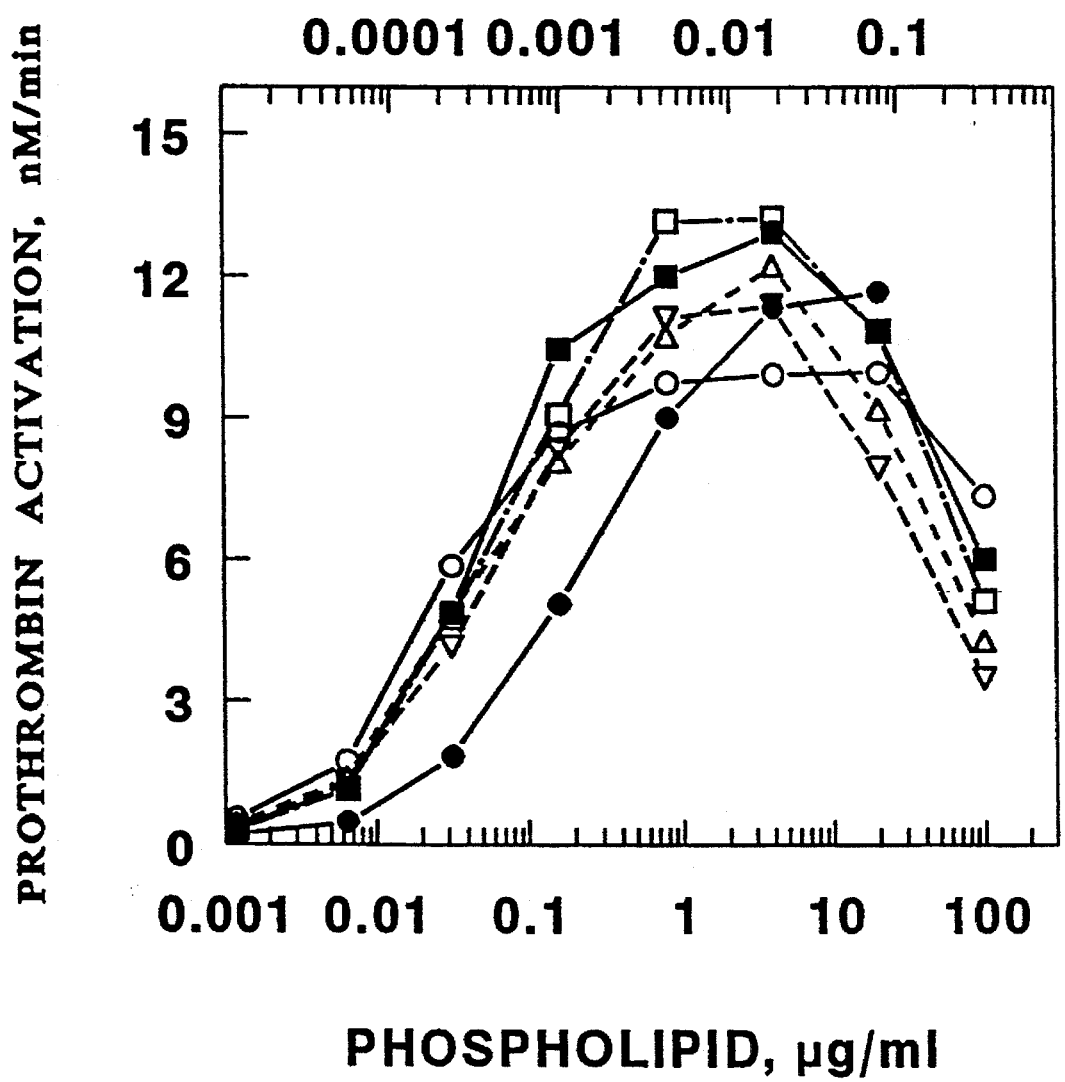
FIGS. 2A and 2B are graphical depiction of data concerning the effect of PE content on liposome activity in prothrombin activation (FIG. 2A) and in inactivation of Factor $V_a$ by APC (FIG. 2B) where open circles, 20% PS/80% PC; open upward pointing triangles, 10% PE/20% PS/70% PC; open downward pointing triangles, 20% PE/20% PS/60% PC; open squares, 30% PE/20% PS/50% PC; closed squares, 40% PE/20% PS/40% PC; closed circles, bovine brain cephalin.
Figure 2B:
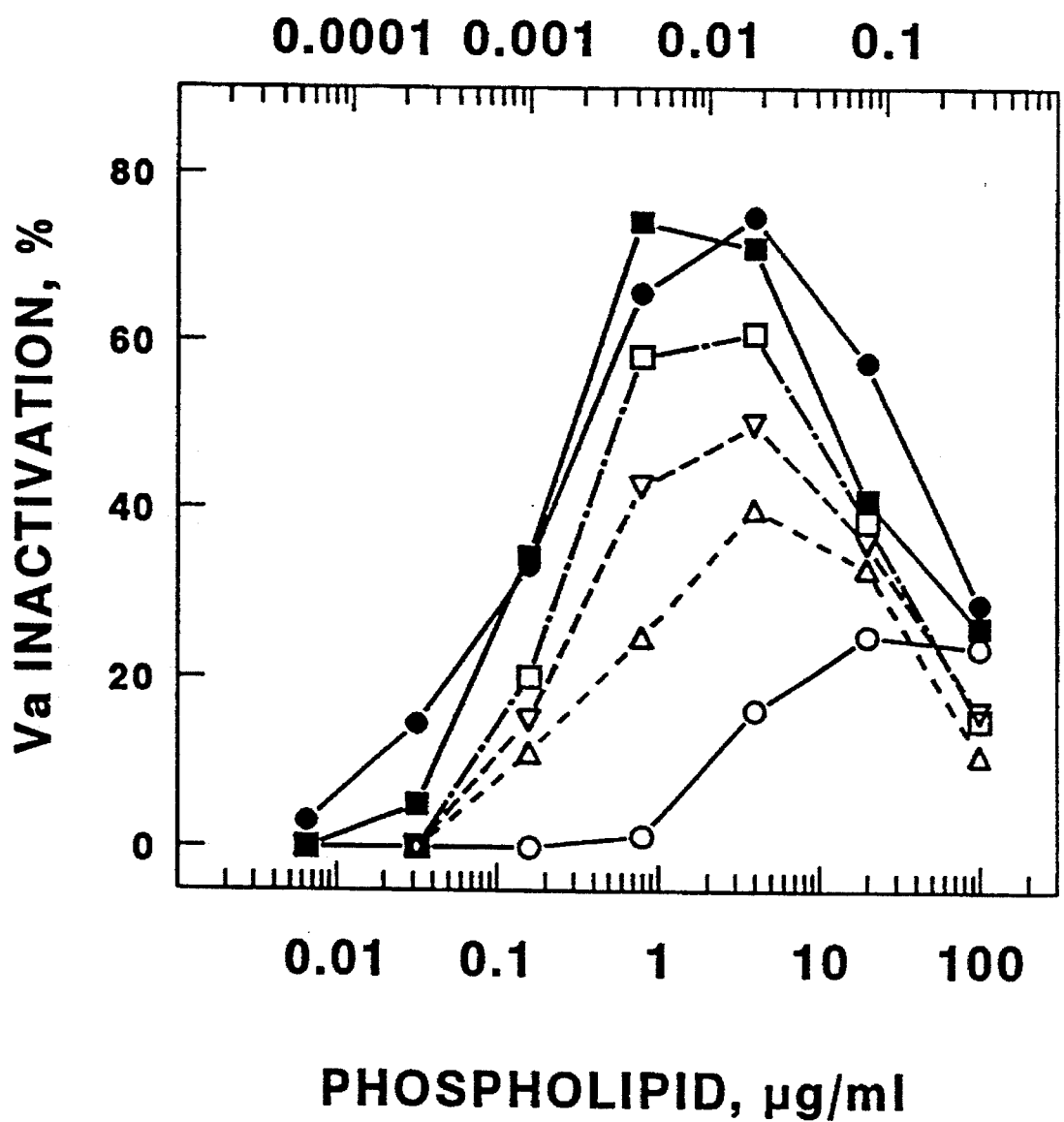

The influence of PE content on prothrombinase activity (FIG. 2A) and on Factor $V_a$ inactivation by APC (FIG. 2B) was studied as a function of phospholipid concentration. There was little influence of PE on the rate of prothrombin activation. Prothrombin activation rates increased as a function of increasing phospholipid concentration with all phospholipid mixtures, but subsequently declined at excess phospholipid. In contrast, APC dependent Factor $V_a$ inactivation was enhanced in proportion to the PE content of the vesicles containing up to 40% PE, the highest concentration compatible with stable vesicle formation. As with prothrombin activation, higher phospholipid concentrations inhibited Factor $V_a$ inactivations. Vesicles with 40% PE were as effective as crude brain cephalin in supporting Factor $V_a$ inactivation.

When analyzed by electron microscopy, the PE containing vesicles were much larger (150 nm) than those without PE (PS/PC≈20 nm) and therefore, to determine if vesicle size could be responsible for the differences, we prepared two sets of large vesicles, one by dialysis from detergent solution and another by extrusion of phospholipid suspensions. The ability to support prothrombinase and APC activities were compared.

Figure 3:
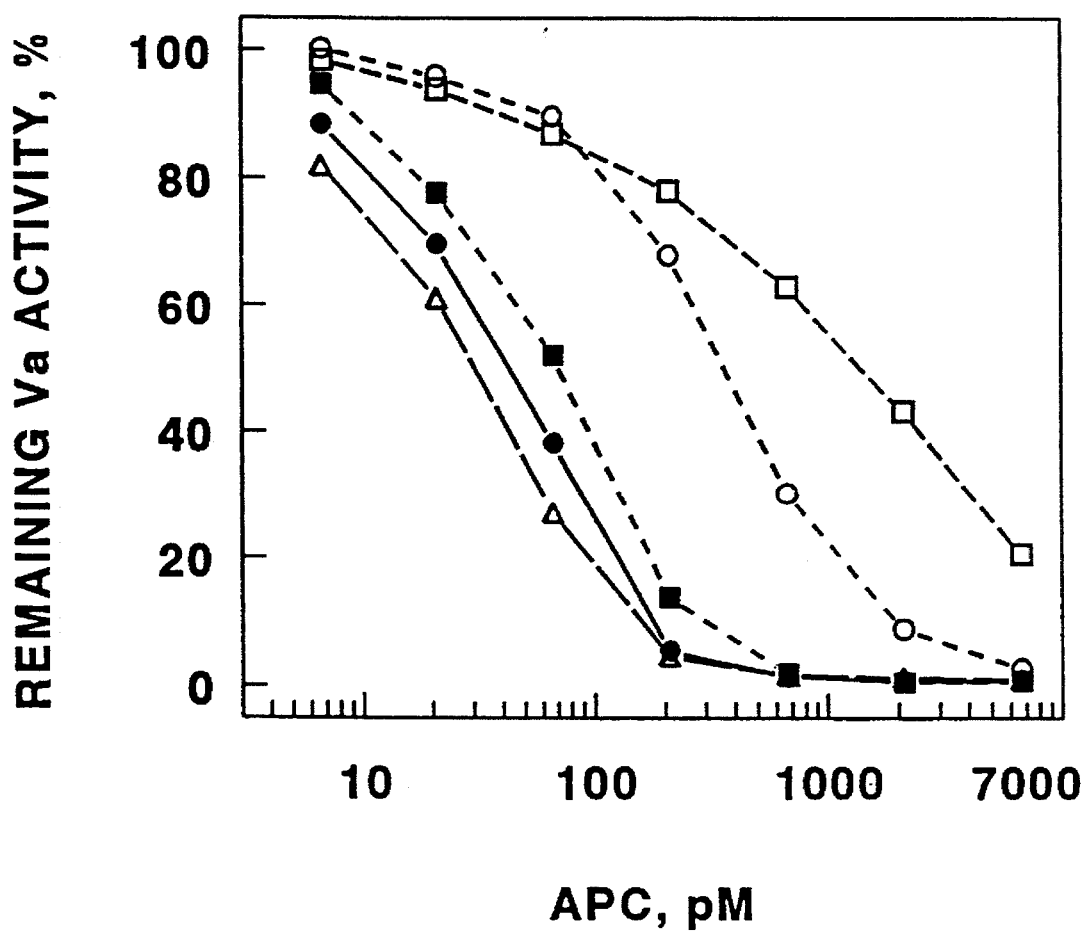
FIG. 3 is a graphical depiction of data concerning the effect of PE on inactivation of Factor $V_a$ on large and small phospholipid vesicles where phospholipid concentration was 4 µg/ml; sonicated vesicles; open circles, 20% PS/80% PC; closed circles, 40% PE/20% PS/40% PC; large dialyzed vesicles; open squares, 20% PS/80% PC; closed squares, 40% PE/20% PS/40% PC; open triangle, bovine brain cephalin.

LV composed of 20% PS/80% PC were ≈250 nm with some multilamellar characteristics as judged from the electron micrographs were made. LV that contained 40% PE/20%P S/40% PC gave particles about 150 nm with less multilamellar character. To support prothrombinase equivalently, approximately a 5 fold higher concentration of phospholipid was needed with LV lacking PE than for those containing PE, possibly reflecting less available surface on a weight basis. Even at 100 times greater concentrations, however, LV lacking PE could not support APC dependent Factor Va inactivation as well as those that contained PE. Thus, vesicle size does not account for the difference in activity. This point is illustrated further in FIG. 3. Extruded vesicles gave qualitatively similar results.

The possible contribution of unsaturated fatty acids was examined also. Bovine brain cephalin (Sigma Chemical Co.) was prepared according to manufacturer's instructions. Bovine brain PE contains about 40% unsaturated and 60% saturated fatty acids. We made sonicated vesicles containing 40% dioleoyl or dilinoleoyl PE. Relative to brain PE, these vesicles increased prothrombin activation about 30%, but did not affect APC activity in the presence of protein S.

The earlier studies were all performed at very low Factor $V_a$ concentrations. To insure that this observation was not unique to these conditions, Factor $V_a$ concentration was increase to 1 nM. Factor $V_a$ inactivation was still enhanced approximately 10 fold by PE containing liposomes (FIG. 3) compared to PE deficient liposomes which is similar to the enhancement seen at lower Factor $V_a$ concentration. As described above, large dialyzed vesicles containing PE were as effective as small vesicles at all APC concentrations in Factor $V_a$ inactivation, but large vesicles containing only PS and PC were slightly less active than the small vesicles. Under these conditions, protein S increased Factor $V_a$ inactivation about 10 fold independently of whether the PS containing vesicles also contain PE. Similar PE dependent enhancement in Factor $V_a$ inactivation was observed even at 10, 100, and 1000 nM Factor $V_a$.

We claim:

1. A method for testing a patient plasma sample for indications of a propensity for thrombotic disease, comprising the steps of:

(a) measuring a first clotting time for a first aqueous reaction mixture comprising a first aliquot of a citrated patient plasma sample in the presence of activated Protein C and a membrane source comprising a phospholipid component comprising an effective amount of phosphatidylethanolamine to allow clotting differences to be detected between normal plasma and plasma from patients with a thrombotic propensity, and an effective amount of phosphatidylserine to complement the function of said phosphatidylethanolamine in a clotting assay;

(b) measuring a second clotting time for a second aqueous reaction mixture comprising a second aliquot of said citrated patient plasma sample, in the presence of a membrane source comprising a phospholipid component comprising an effective amount of phosphatidylethanolamine to allow clotting differences to be detected between normal plasma and plasma from patients with a thrombotic propensity and an effective amount of phosphatidylserine to complement the function of said phosphatidylethanolamine in a clotting assay, and in the absence of activated Protein C;

(c) measuring a third clotting time for a third aqueous reaction mixture comprising a first aliquot of a control plasma sample in the presence of activated Protein C and a membrane source comprising a phospholipid component comprising an effective amount of phosphatidylethanolamine to allow clotting differences to be detected between normal plasma and plasma from patients with a thrombotic propensity and an effective amount of phosphatidylserine to complement the function of said phosphatidylethanolamine in a clotting assay;

(d) measuring a fourth clotting time for a fourth aqueous reaction mixture comprising a second aliquot of said control plasma in the presence of a membrane source comprising a phospholipid component comprising an effective amount of phosphatidylethanolamine to allow clotting differences to be detected between normal plasma and plasma from patients with a thrombotic propensity and an effective amount of phosphatidylserine to complement the function of said phosphatidylethanolamine in a clotting assay, and in the absence of activated Protein C;

(e) comparing said first, second, third and fourth clotting times and denoting said patient to be at risk for thrombosis if said first clotting time is less than said third clotting time, and said second clotting time is greater than or equal to said fourth clotting time at an optimal phospholipid concentration.

2. The method of claim 1, wherein said membrane source further comprises phosphatidylcholine in an amount sufficient to bring said phospholipid component of said membrane source to 100%.

3. The method of claim 1, wherein said phospholipid component of said membrane source comprises about 40% phosphatidylethanolamine, about 20% phosphatidylserine and about 40% phosphatidylcholine.

4. The method of claim 1, wherein said effective amount of phosphatidylethanolamine is from about 10 to about 50% by weight of said phospholipid component of said membrane source and wherein said effective amount of phosphatidylserine is from about 5 to about 50% by weight of said phospholipid component of said membrane source.

5. The method of claim 1, wherein said effective amount of said phosphatidylethanolamine is from about 10 to about 50% by weight of said phospholipid component of said membrane source, and said phosphatidylserine is from about 5 to about 25% of said phospholipid component of said membrane source.

6. The method of claim 1, 2, 3, 4, or 5 wherein said clotting times are determined in said aqueous reactions mixtures by an aqueous chromogenic method.

7. The method of claim 1, 2, 3, 4, or 5, wherein said clotting times are determined by visual observation of clot formation in said aqueous reaction mixtures.

8. The method of claim 1, 2, 3, 4 or 5, wherein said clotting times are determined by using instrumentation adapted to detection of clotting.

9. The method of claim 8, wherein said instrumentation is an automatic plate reader equipped with spectrophotometric capabilities for monitoring reaction mixtures at a wavelength appropriate to detect a clotting reaction.

10. The method of claim 8 wherein said clotting times in said aqueous reaction mixtures are determined by an aqueous chromogenic method.

11. The method of claim 8, wherein said clotting times are determined by detection of changes in turbidity in said aqueous reaction mixtures over time.

12. A method for testing a patient plasma sample for indications of a propensity for thrombotic disease, comprising the steps of:

(a) measuring a first clotting time for a first aqueous reaction mixture comprising a first aliquot of a citrated patient plasma sample in the presence of activated Protein C, a volume of normal plasma in an amount about equal to said aliquot of a citrated plasma sample, and a membrane source comprising a phospholipid component comprising an effective amount of phosphatidylethanolamine to allow clotting differences to be detected between normal plasma and plasma from patients with a thrombotic propensity and an effective amount of phosphatidylserine to complement the function of said phosphatidylethanolamine in a clotting assay;

(b) measuring a second clotting time for a second aqueous reaction mixture comprising a second aliquot of said citrated patient plasma sample, in the presence of a membrane source comprising a phospholipid component comprising an effective amount of phosphatidylethanolamine to allow clotting differences to be detected between normal plasma and plasma from patients with a thrombotic propensity and an effective amount of phosphatidylserine to complement the function of said phosphatidylethanolamine in a clotting assay, and a volume of normal plasma in an amount about equal to said aliquot of a citrated plasma sample, and in the absence of activated Protein C;

(c) measuring a third clotting time for a third aqueous reaction mixture comprising a first aliquot of a control plasma sample in the presence of activated Protein C, and a membrane source comprising a phospholipid component comprising an effective amount of phosphatidylethanolamine to allow clotting differences to be detected between normal plasma and plasma from patients with a thrombotic propensity and an effective amount of phosphatidylserine to complement the function of said phosphatidylethanolamine in a clotting assay;

(d) measuring a fourth clotting time for a fourth aqueous reaction mixture comprising a second aliquot of said control plasma in the presence of a membrane source comprising a phospholipid component comprising an effective amount of phosphatidylethanolamine to allow clotting differences to be detected between normal plasma and plasma from patients with a thrombotic propensity and an effective amount of phosphatidylserine to complement the function of said phosphatidylethanolamine in a clotting assay, and in the absence of activated Protein C;

(e) comparing said first, second, third and fourth clotting times and denoting said patient sample to be at risk for thrombosis if said first clotting time is less than said third clotting time, and said second clotting time is greater than or equal to said fourth clotting time, at an optimal phospholipid concentration.

13. The method of claim 12, wherein said membrane source further comprises phosphatidylcholine in an amount sufficient to bring said phospholipid component of membrane source to 100%.

14. The method of claim 12, wherein said phospholipid component of said membrane source comprises about 40% phosphatidylethanolamine, about 20% phosphatidylserine and about 40% phosphatidylcholine.

15. The method of claim 12, wherein said effective amount of phosphatidylethanolamine is from about 10 to about 50% by weight of said phospholipid component of said membrane source and wherein said effective amount of phosphatidylserine is from about 5 to about 50% by weight of said phospholipid component of said membrane source.

16. The method of claim 12, wherein said effective amount of said phosphatidylethanolamine is from about 10 to about 50% by weight of said phospholipid component of said membrane source, and said phosphatidylserine is from about 5 to 25% of said phospholipid component of said membrane source.

17. The method of claim 12, 13, 14, 15, or 16, wherein said clotting times are determined by visual observation of clot formation in said aqueous reaction mixtures.

18. The method of claim 12, 13, 14, 15 or 16 wherein said clotting times are determined by using instrumentation adapted to detection of clotting.

19. The method of claim 18, wherein said instrumentation is an automatic plate reader equipped with spectrophotometric capabilities for monitoring reaction mixtures at a wavelength appropriate to detect a clotting reaction.

20. The method of claim 19, wherein said clotting times in said aqueous reaction mixtures are determined by an aqueous chromogenic method.

21. The method of claim 18 wherein said clotting times in said aqueous reaction mixtures are determined by an aqueous chromogenic method.

22. A method for monitoring the effectiveness of antiinflammatory drug or anticoagulant therapy in lupus anticoagulant patients or patients with antiphospholipid antibodies, comprising the steps of:

(a) forming a first citrated plasma sample from a blood sample obtained from said patients at a first time;

(b) testing said first citrated plasma sample for coagulation properties in the presence and absence of activated Protein C and in the presence of a membrane source comprising a phospholipid component comprising an effective amount of phosphatidylethanolamine to allow clotting difference to be observed between normal plasma and patients with thrombotic propensities and an effective amount of phosphatidylserine to complement the function of said phosphatidylethanolamine in a clotting assay, and comparing said coagulation properties of said first citrated plasma sample to control plasma to obtain a first result;

(c) repeating step (b) on a second sample of citrated plasma obtained from said patient at a second time to obtain a second result;

(d) determining said therapy to be providing a desired effect if, in the presence of activated protein C, said second result indicates said second citrated plasma sample takes more time to clot than said first citrated plasma sample and if, in the absence of activated protein C, said second citrated plasma sample takes less than or equal time to clot compared to said first citrated plasma sample.

23. The method of claim 22, wherein said membrane source further comprises phosphatidylcholine in an amount sufficient to bring said phospholipid component of said membrane source to 100%.

24. The method of claim 22, wherein said phospholipid component of said membrane source comprises about 40% phosphatidylethanolamine, about 20% phosphatidylserine and about 40% phosphatidylcholine.

25. The method of claim 22, wherein said effective amount of phosphatidylethanolamine is from about 10 to about 50% by weight of said phospholipid component of said membrane source and wherein said effective amount of phosphatidylserine is from about 5 to about 50% by weight of said phospholipid component of said membrane source.

26. The method of claim 22, wherein said effective amount of said phosphatidylethanolamine is from about 10 to about 50% by weight of said phospholipid component of said membrane source, and said effective amount of phosphatidylserine is from about 5 to about 25% of said phospholipid component of said membrane source.

27. The method of claims 22, 23, 24, 25, or 26, wherein said citrated plasma samples obtained from said patients are mixed with an equal volume of normal plasma prior to said testing for coagulation properties.

28. A method for testing a patient plasma sample for indications of a propensity for thrombotic disease, comprising the steps of:

(a) mixing in a first reaction chamber a phospholipid membrane source comprising at least 10% phosphatidylethanolamine and at least 5% phosphatidylserine, activated Protein C, a coagulation initiator, and a patient citrated plasma sample;

(b) mixing in a second reaction chamber a phospholipid membrane source comprising at least 10% phosphatidylethanolamine and at least 5% phosphatidylserine, activated Protein C, a coagulation activator, and a normal control plasma sample;

(c) mixing in a third reaction chamber a phospholipid membrane source comprising at least 10% phosphatidylethanolamine and at least 5% phosphatidylserine, a coagulation activator, and a patient citrated plasma sample;

(d) mixing in a fourth reaction chamber a phospholipid membrane source comprising at least 10% phosphatidylethanolamine and at least 5% phosphatidylserine, a coagulation activator, and a normal control plasma sample; and (e) adding an effective amount of $Ca^{2+}$ to each of said first, second, third and fourth reaction chamber to initiate clotting; and (f) observing the amount of time it takes for the mixture in each of said first, second, third and fourth reaction chambers to form a clot, and if the time for said first mixture to clot is less than the time for said second mixture to clot and the time for said third mixture to clot is greater than or equal to the time for said fourth mixture to clot, concluding that said patient plasma sample is indicative of a propensity for thrombic disease.

29. The method of claim 28, wherein prior to step (e), an equal amount of a normal control citrated plasma is added to each of said first, second, third and fourth reaction chambers.

30. The method of claim 28 or 29, wherein said phospholipid membrane source comprises 10–50% phosphatidylethanolamine, 5–50% phosphatidylserine, and the remainder phosphatidylcholine.

31. The method of claim 28 or 29, wherein said phospholipid source comprises about 40% phosphatidylethanolamine, about 20% phosphatidylserine and about 40% phosphatidylcholine.

32. The method of claim 28 or 29, wherein said coagulation initiator is a Factor X-activating enzyme.

33. The method of claim 32, wherein said Factor X-activating enzyme is Russell's viper venom.

34. The method of claim 28 or 29, wherein said coagulation initiator is an activator of the contact system of coagulation.

35. The method of claim 28 or 29, wherein said coagulation initiator is selected from the group consisting of Factor $X_a$, Factor $IX_a$, Factor $XI_a$, and Tissue Factor.

36. The method of claim 28 or 29, wherein said coagulation initiator is Factor $X_a$.

* * * * *